US009480759B2

(12) United States Patent
Stevenson et al.

(10) Patent No.: US 9,480,759 B2
(45) Date of Patent: Nov. 1, 2016

(54) TIN-117M SOMATOSTATIN RECEPTOR BINDING COMPOUNDS AND METHODS

(71) Applicant: Serene Oncology, LLC, New York, NY (US)

(72) Inventors: Nigel R. Stevenson, Sugar Hill, GA (US); Jaime Simon, Angleton, TX (US); Gilbert R. Gonzales, Tucson, AZ (US)

(73) Assignee: Serene, LLC, The Woodlands, TX (US)

( * ) Notice: Subject to any disclaimer, the term of this patent is extended or adjusted under 35 U.S.C. 154(b) by 156 days.

(21) Appl. No.: 14/082,293

(22) Filed: Nov. 18, 2013

(65) Prior Publication Data
US 2014/0140923 A1    May 22, 2014

Related U.S. Application Data

(60) Provisional application No. 61/843,481, filed on Jul. 8, 2013, provisional application No. 61/821,833, filed on May 10, 2013, provisional application No. 61/728,879, filed on Nov. 21, 2012.

(51) Int. Cl.
A61K 51/00     (2006.01)
A61M 36/14     (2006.01)
A61K 51/08     (2006.01)
A61K 51/04     (2006.01)

(52) U.S. Cl.
CPC ......... A61K 51/083 (2013.01); A61K 51/0482 (2013.01)

(58) Field of Classification Search
CPC .... A61K 51/00; A61K 51/08; A61K 51/083; A61K 541/04; A61K 51/0482
USPC ......... 424/1.11, 0.165, 1.69, 9.1, 9.2; 514/1, 514/1.1, 11.1, 19.2, 19.3; 530/300, 311; 534/10
See application file for complete search history.

(56) References Cited

U.S. PATENT DOCUMENTS

| 8,257,681 B2 * | 9/2012 | Stevenson ................. G21G 1/10 424/1.11 |
| 2004/0136907 A1 * | 7/2004 | DeJong et al. ............... 424/1.49 |
| 2012/0213698 A1 * | 8/2012 | Petersen et al. .............. 424/1.37 |

FOREIGN PATENT DOCUMENTS

| EP | 0714911 A2 | 6/1996 |
| WO | 9500553 A1 | 1/1995 |
| WO | 0181426 A2 | 11/2001 |
| WO | 2006094725 A1 | 9/2006 |

OTHER PUBLICATIONS

Srivastava et al, Clinical Cancer Research, 1998, vol. 4, pp. 61-68.*
Srivastava, SC, "Paving the Way to Personalized Medicine: Production of Some Promising Theragnostic Radionuclides at Brookhaven National Laboratory", Seminars in Nuclear Medicine, vol. 42, No. 3, May 1, 2012, pp. 151-163 [XP055098789].
International Search Report and Written Opinion from the International Searching Authority of the European Patent Office, issued in corresponding PCT Application No. PCT/US2013/070514, dated Feb. 5, 2014 (12 pages).

* cited by examiner

Primary Examiner — D L Jones
(74) Attorney, Agent, or Firm — Wood Herron & Evans LLP

(57) ABSTRACT

Tin-117m somatoostatin analogs or antagonist are used to treat tumors and symptoms associated with these tumors which express somatostatin receptors, such as gastroenteropancreatic neuroendocrine tumors. The tin-117m somatostatin receptor binding compounds can be administered at a dosage which is effectively apoptotic and not necrotic. Also, if desired, it can be administered at a dose that is necrotic and/or induces necrosis, but only to cells within 290 microns of the tin-117m atom. A novel somatostatin analog is also disclosed, as well as novel methods to produce the tin labeled analogs and antagonists.

11 Claims, 5 Drawing Sheets

TIN-117M SOMATOSTATIN RECEPTOR BINDING COMPOUNDS AND METHODS

PRIORITY CLAIM

This application is based on provisional patent application U.S. Ser. No. 61/728,879, filed Nov. 21, 2012; U.S. Ser. No. 61/821,833, filed May 10, 2013; and U.S. Ser. No. 61/843,481, filed Jul. 8, 2013, the disclosures of which are incorporated herein by reference and priority to which each application is claimed.

BACKGROUND OF THE INVENTION

The primary treatment for Gastroenteropancreatic Neuroendocrine tumors (GEP-NETS), such as carcinoid tumors, is surgery with curative intent. However, in many patients this is often impossible and alternatives such as external beam radiation or chemotherapy are sub-optimal because these well-differentiated tumors are relatively unresponsive. Most of these tumors express somatostatin receptors, especially sub-type 2, in high abundance, which very rapidly bind and internalize targeted peptides. Other cancers, such as ovarian cancer, also exhibit somatostatin receptors.

Somatostatin analogues, such as lanreotide and octreotide, as well as octreotate, have been tested as a means to deliver a radioisotope to the cancerous tissue. Generally, the somatostatin peptide analogues are coupled with a complexing agent such as DOTA (1,4,7,10-tetra-azacyclododecane-N,N',N'',N'''-tetraacetic acid). Other complexing moieties are disclosed for example in PCT/EP01/08824. Both Yttrium-90 and Lutetium-177 have been used to deliver a tumoricidal radiation dose. Lutetium is a medium energy beta emitter with a maximum tissue penetration of 1.6 mm and a physical half life of 6.7 days. It also emits medium and low energy gamma radiation. But the gamma radiation provides very poor resolution for imaging purposes. Gallium-68 is a positron emitter and has been used for imaging, but has limited therapeutic benefit. However, none of these radioisotopes are optimal from a therapeutic perspective.

Depending on the delivery system and mode of elimination from the body, some beta emitters can adversely affect the kidneys and other organs, and some alpha emitters create systemic problems such as gastrointestinal and pulmonary adverse events. Further, many alpha emitters cannot be imaged.

SUMMARY OF THE INVENTION

The present invention is premised on the realization that tumors with somatostatin receptors can be effectively imaged and treated with tin-117m labeled somatostatin receptor binding compounds, including somatostatin analogues (agonists) as well as somatostatin antagonists.

In particular, such tumors can be treated with tin-117m labeled octreotate(tyr$^3$), such as tin-117m bonded to DOTA-TATE. Further, a lysine modified octreotate(tyr$^3$) referred to as nonatate can also be used.

The invention further includes methods of bonding the tin-117m to the octreotate or modified octreotate which can be directly applied to other somatostatin receptor binding compounds.

The present invention is further premised on the realization that tumors with somatostatin binding sites can be effectively imaged and treated with tin-117m labeled somatostatin antagonists such as BASS, which has the following general formula, Ac-4-NO$_2$-Phe-c(D-Cys-Tyr-D-Trp-Lys-Thr-Cys)-D-NH$_2$, as well as J11. In particular, such tumors can be treated with tin-117m labeled BASS or J11, and, in particular, tin-117m bonded to DOTA-BASS or DOTA-J11.

The objects and advantages of the present invention will be further appreciated in light of the following detailed description.

DETAILED DESCRIPTION

According to the present invention, tin-117m held by a binding moiety is attached to a somatostatin receptor binding compound such as a somatostatin analogue agonists or antagonist. In turn, these compounds effectively treat tumors having somatostatin receptors.

Tin-117m is a radioisotope which emits strong conversion electrons which travel about 290 microns in tissue. Thus, it has a very defined effective distance. Tin-117m can be prepared in an accelerator such as a cyclotron by transmutation of antimony into no-carrier-added tin-117m by high energy proton induced nuclear reactions. No-carrier-added tin-117m can also be obtained by exposing cadmium 116 to an alpha particle beam as described in U.S. Pat. No. 8,257,681, the disclosure of which is incorporated herein by reference. This permits formation of high specific activity tin-117m preferably having 100 to 1000 or more curies per gram.

Binding moieties such as DOTA are commercially available, as are somatostatin analogue peptides such as octreotate(tyr$^3$). These are further disclosed in EP 0714911 and GB-A-2,225,579. Further, somatostatin antagonists such as BASS and J11 are known.

For use in the present invention, any somatostatin analogue or direct antagonist can be used. Known analogues include lanreotide, octreotide and octreotate, as well as nonatate. Examples 1 and 2 disclose the preparation of octreotate and nonatate for use in the present invention.

Example 1

Preparation of Protected Octreotate

Protected octreotate was prepared by Solid Phase Peptide Synthesis using standard reagents. The structure of the product was: H2N-dPhe-Cys-Tyr(tBu)-dTrp(Boc)-Lys(Boc)-Thr(tBu)-Cys-Thr(tBu)-COOH with a disulfide bridge between the two Cys. The purity was >95%. This was confirmed by HPLC. The molecular weight was calculated to be 1416.4 Daltons. MS confirmed this with an ion mass of 1417 m/z.

Example 2

Preparation of Protected Nonatate

Protected octreotate was prepared by Solid Phase Peptide Synthesis using standard reagents. The structure of the product was: Boc-Lys(ε-NH2)-dPhe-Cys-Tyr(tBu)-dTrp(Boc)-Lys(Boc)-Thr(tBu)-Cys-Thr(tBu)-COOH with a disulfide bridge between the two Cys. The purity was >95%. This was confirmed by HPLC. The molecular weight was calculated to be 1645 Daltons. MS confirmed this with an ion mass of 1645 m/z.

The somatostatin analogue is bound to the tin-117m using a stable chelating or binding molecule such as DOTA. The DOTA reacts with the terminal amino acid on the peptide. Although as disclosed hereinafter, any method can be used to bind the DOTA to the somatostatin analogue.

Figure 1:
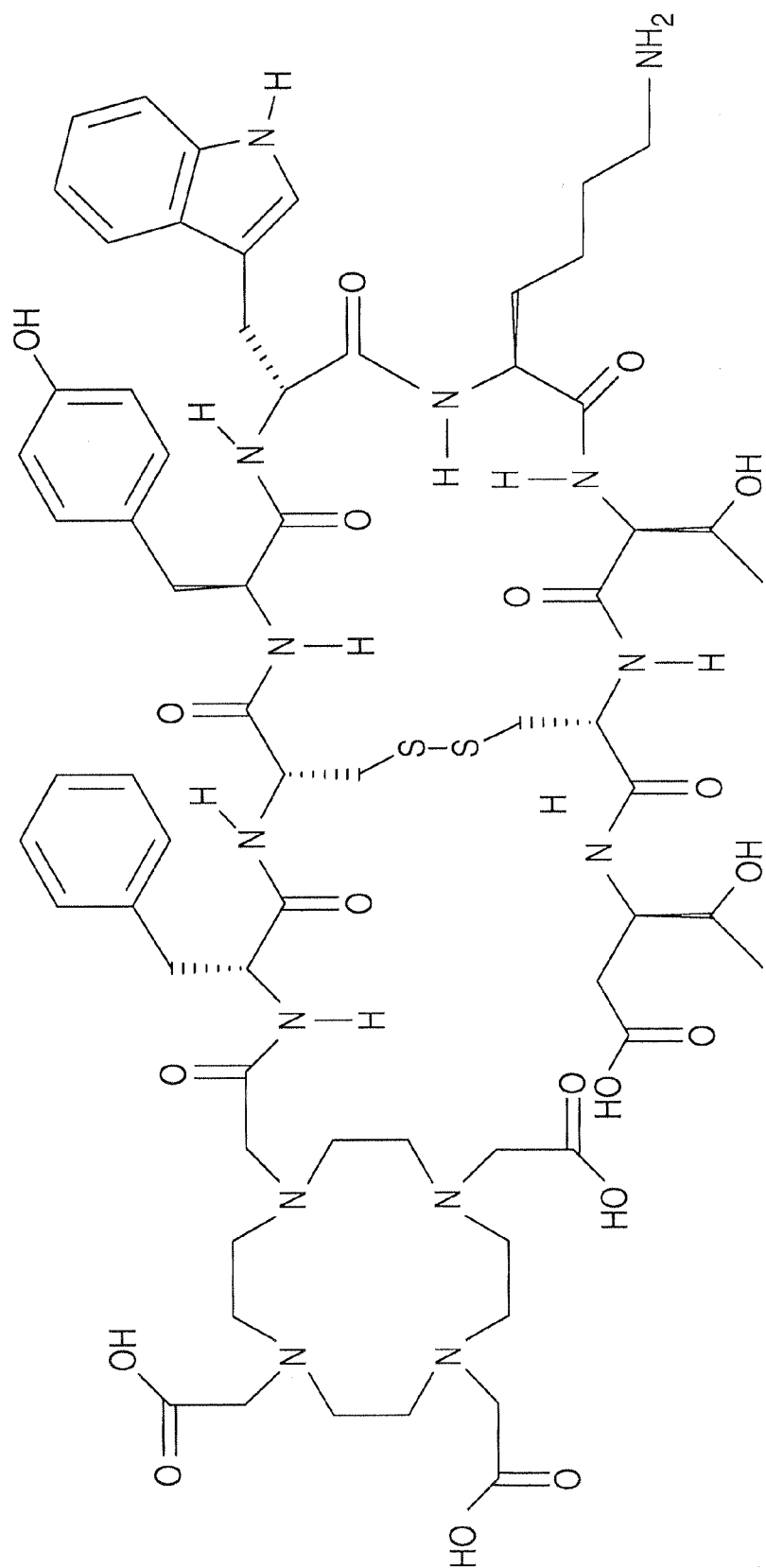
FIG. 1 is a drawing of DOTA-3 octreotate(tyr$^3$) or DOTATATE.
Figure 2:
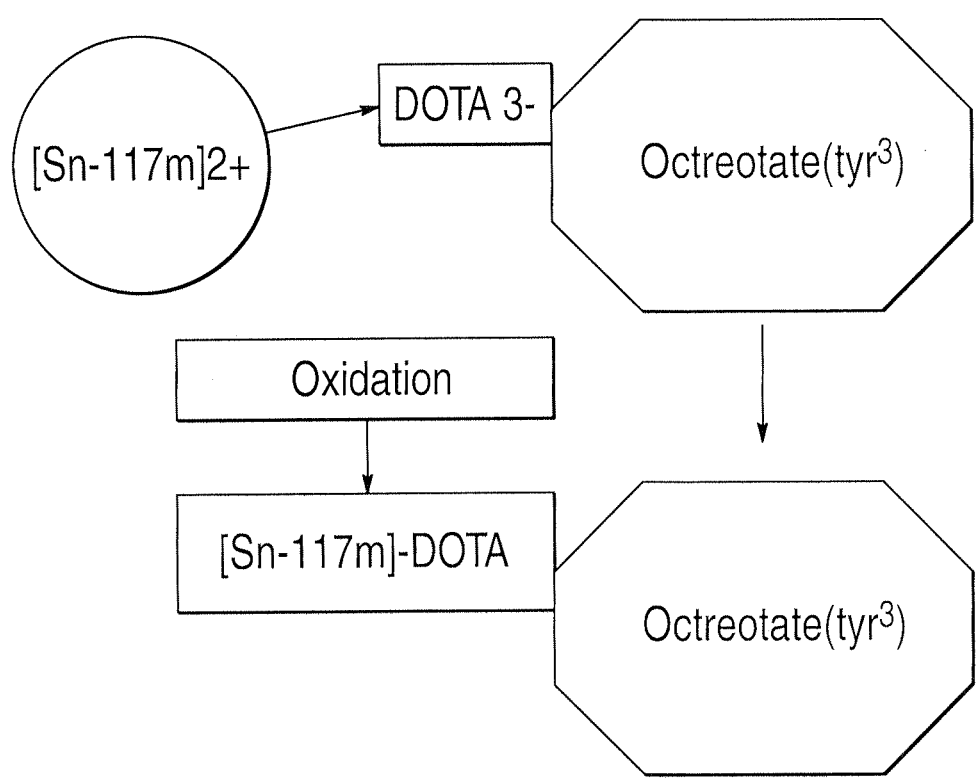
FIG. 2 is a schematic depiction of a first reaction scheme.

As shown in FIG. 2, Tin-117m in the +2 state can be reacted with DOTA-3 octreotate(tyr$^3$). DOTA-3 is DOTA with 3 available carboxylic acid groups. The reaction is simply conducted by mixing the DOTA-TATE shown in FIG. 1 with the tin-117m in the +2 state at room temperature to about 90° C. at pH about 5. The tin$^{+2}$ chelates to the DOTA-3. The tin$^{+2}$ oxidizes to tin$^{+4}$ over time or the process can be accelerated by bubbling oxygen through the solution. The tin-117m will thereby remain chelated to the DOTA-3. This may be purified with HPLC to extract the tin-117m DOTA-TATE. This is further shown in the following two examples.

Example 3

Preparation of Sn-DOTA-TATE (Non-Radioactive)

A 0.1 M solution of HCl was prepared by diluting 1.25 mL of 4 M HCl to 50 mL using deionized water. Into this was dissolved 9.48 mg of commercially available stannous chloride (SnCl2, 189.6 mg/mmole) to produce a 0.001 M solution of Sn(II).

Into a plastic microcentrifuge tube was placed 28 μL of the 0.001 M Sn(II) solution. To this was added 200 μL of commercially available DOTA-TATE solution (Bachem). The pH was adjusted to 6 by the gradual addition of a pH 7 sodium bicarbonate solution. The reaction was allowed to proceed for 1 hour at room temperature and then placed in a refrigerator. HPLC-MS was used to track the reaction from 1 hour through 48 hours. The chromatographic retention times were as expected. The loss of the DOTA-TATE mass at 1435 m/z and the growth of the product peak Sn-DOTA-TATE mass at 1550 m/z was confirmed. The Sn(II) oxidized to Sn(IV) to form a final product of Sn(IV)-DOTA-TATE Example 4

Preparation of 117mSn-DOTA-TATE

Radioactive 117mSn(II) was reacted with commercial DOTA-TATE under the same conditions as in Example 3. The product $^{117m}$Sn-DOTA-TATE was confirmed using HPLC-UV. The Sn(II) oxidized to $^{117m}$Sn(IV) to form a final product of Sn(IV)-DOTA-TATE.

Figure 3:
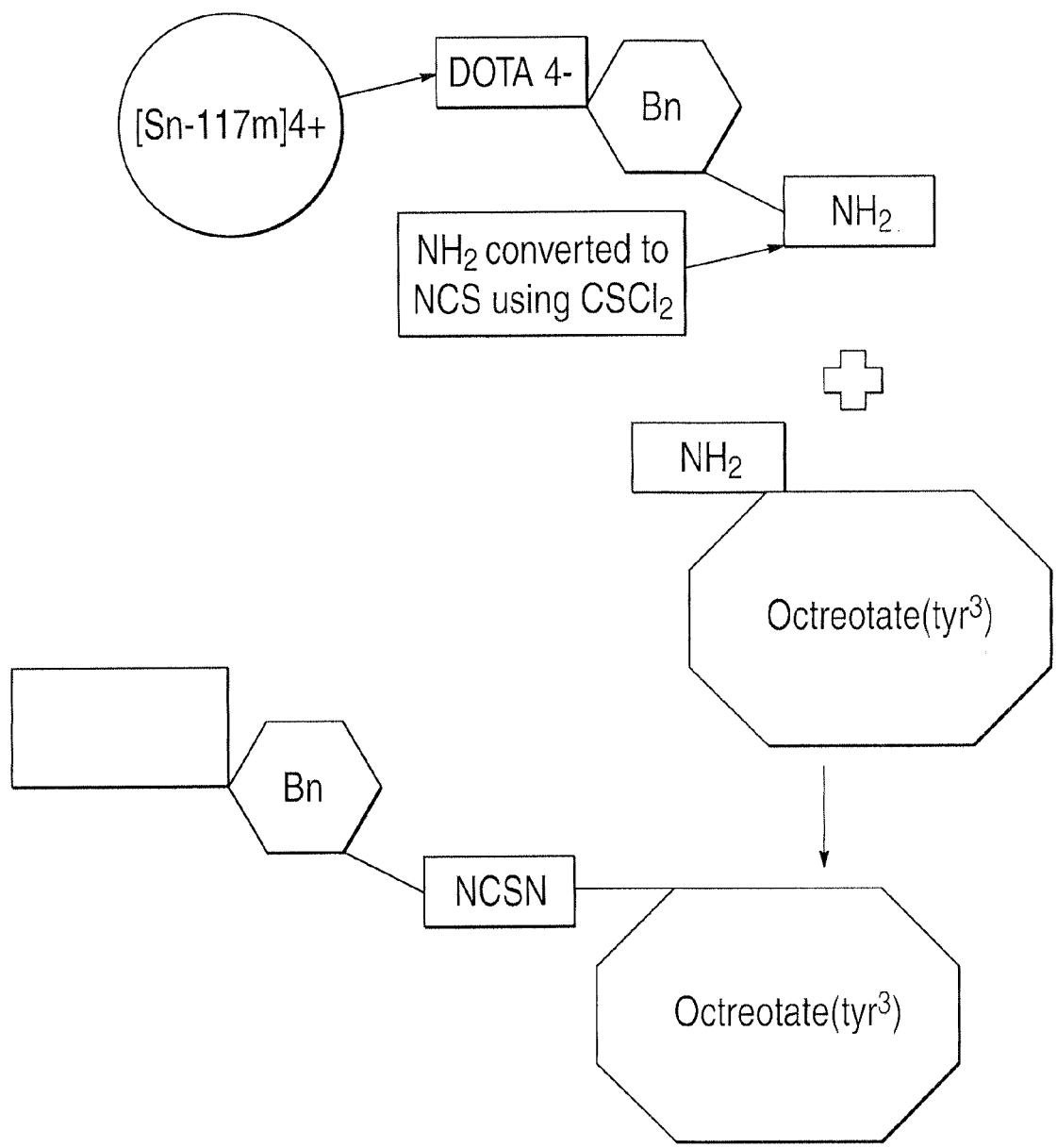
FIG. 3 is a schematic depiction of a second reaction scheme.

DOTA-TATE can also be formed by the method outlined in FIG. 3. This reaction utilizes aminobenzyl DOTA-4 to bind tin$^{+4}$ to the octreotate(tyr$^3$). The DOTA-4 has all four carboxylic acid groups available to bind to tin. As shown in the chart, Method 2, tin-117m in the +4 state is reacted with aminobenzyl DOTA at elevated temperatures, about 140° C., for 15 minutes to bind the tin to the DOTA-4. This can be conducted in a microwave. The mixture is then purified using HPLC and the tin-117m aminobenzyl DOTA is reacted with thiophosgene to convert the amine to a thiocyanate.

The octreotate(tyr$^3$) is modified by adding an amine group to position 1 of the octreotate. This compound is mixed with the tin-117m-isothiocyanotobenzyl DOTA and the pH adjusted to about 9. The mixture is heated at 35-40° C. for 1-2 hours to form tin-117m-benzyl-NCSN-DOTA-TATE. This can then be purified further with HPLC. This is further elaborated in the following two examples.

Example 5

Preparation of 117mSn-IBD

A solution of commercially available aminobenzyl-DOTA (ABD, 100 μL, 20 mg/mL, Macrocyclics) was combined with solid $^{117m}$SnCl$_4$ in a glass vial (Biotage, 2-5 mL) containing a magnetic stir bar. The volume was increased to 2 mL by the addition of water. The vial was sealed, stirred for 30 min at room temperature and was then heated to 140° C. for 15 min in a Biotage Initiator Microwave Synthesizer.

After cooling, the $^{117m}$Sn-ABD complex was purified using prep-HPLC (Altima C18, 0.05% TFA gradient to acetonitrile). The product peak was collected and concentrated by heating under a stream of N$_2$ to 0.5 mL.

The 117mSn-ABD was converted to $^{117m}$Sn-IBD by the addition of 0.2 μL thiophosgene to form the isothiscyanate product. Excess thiophosgene was removed by extracting with diethyl ether (4×2 mL). Completion of reaction was confirmed using HPLC-UV/Rad.

Example 6

Preparation of 117mSn-IBD Octreotate

Into a plastic microcentrifuge tube was placed 1 mg of the protected octretotate from Example 1. This was dissolved in acetonitrile (100 μL). The pH was adjusted to about 9 using triethylamine. To this was added $^{117m}$Sn-IBD from Example 5. (5 molar excess). The reaction mixture was heated to 35° C. for 2 hours. The reaction mixture was removed from the heat and thiohenol (20 μL) was added.

HPLC-UV-RAD-MS was used to confirm successful reaction product (mass 1966 m/z and expected chromatographic retention time).

Octreotate(tyr$^3$) can also be modified by adding lysine at position 1 of the octreotate(tyr$^3$) to produce a 9-peptide amino acid chain with the lysine at position 1. This is referred to as nonatate. The lysine has a free amine group, which can be reacted according to the previous method.

Figure 4:
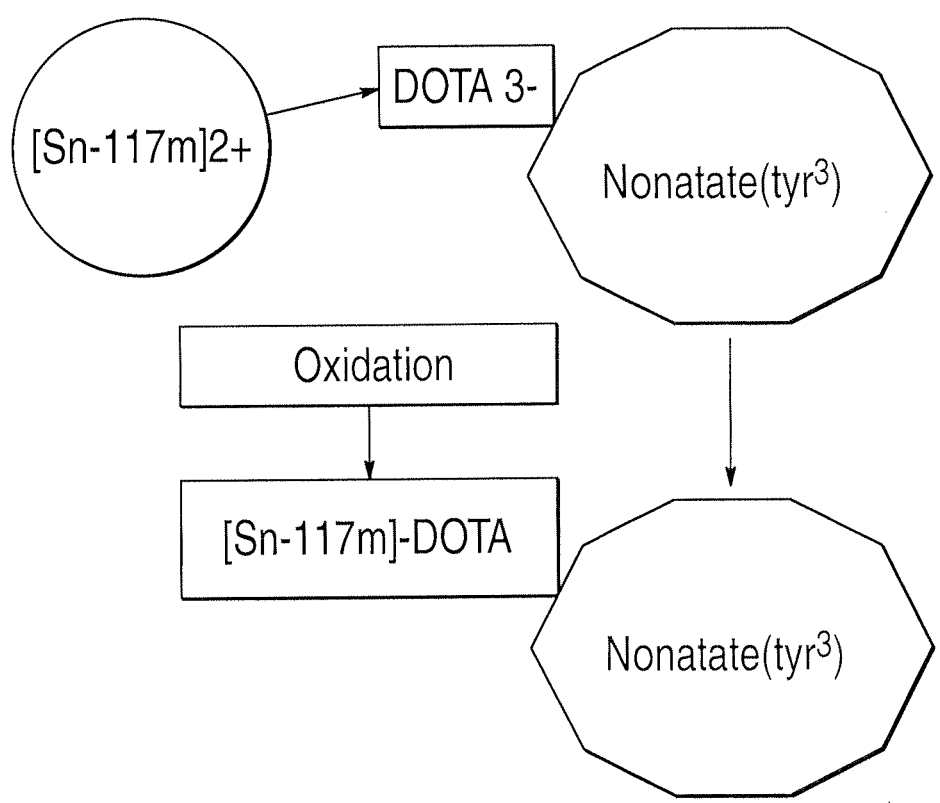
FIG. 4 is a schematic depiction of a third reaction scheme.

According to the reaction scheme shown in FIG. 4, the lysine bonds to DOTA, forming DOTA-3 bonded to the peptide. Tin (II)-117m is reacted with the DOTA-3 at lower temperatures and is subsequently oxidized to tin (IV).

Figure 5:
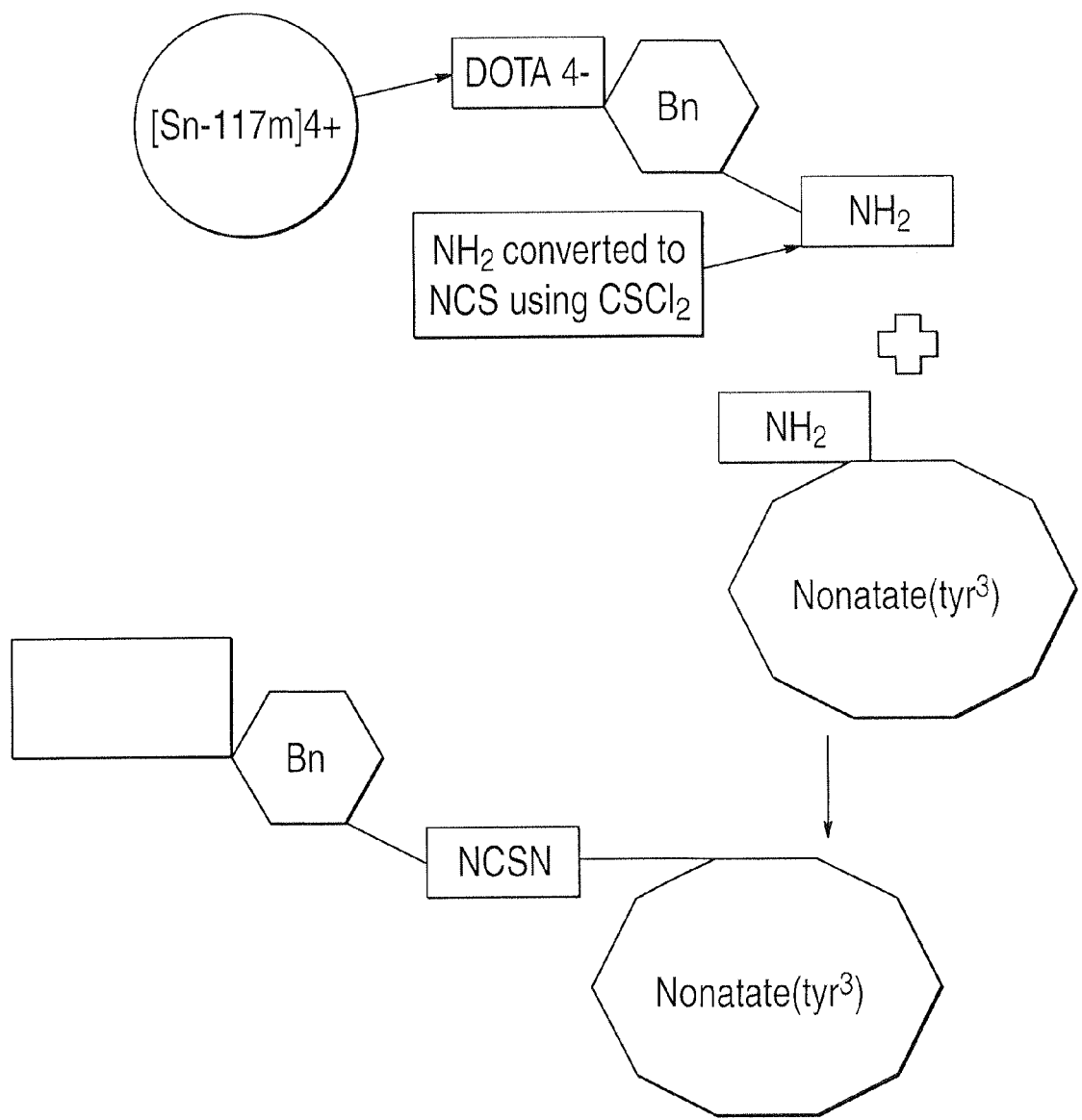
FIG. 5 is a schematic depiction of a fourth reaction scheme.

Alternately, thiophosgene modified amino benzyl DOTA tin (IV)-117m with the nitrogen of the lysine at position 1 of the nonatate. In this reaction, shown in FIG. 5, the lysine of the original octreotate is protected or blocked prior to the DOTA reaction. This is further elaborated in the following example.

Example 7

Preparation of 117mSn-IBD Nonatate

Into a plastic microcentrifuge tube was placed 1 mg of the protected nonatate from Example 2. This was dissolved in acetonitrile (100 μL). The pH was adjusted to about 9 using triethylamine. To this was added $^{117m}$Sn-IBD from Example 5. (5 molar excess) and thiophenol (20 μL). The reaction mixture was heated to 35° C. for 2 hours. The reaction mixture was removed from the heat. HPLC-UV-RAD-MS was used to confirm reaction product.

According to one method, tin-117m in the +2 state can be reacted to a DOTA-3 BASS or DOTA-3 J11. "DOTA-3" represents DOTA with 3 available carboxylic acid groups. The reaction is simply conducted by mixing the DOTA-BASS or DOTA-J11 with the tin-117m in the +2 state at room temperature to about 90° C. The tin$^{+2}$ chelates to the DOTA-3. The tin$^{+2}$ is oxidized by oxygen in the solution to tin$^{+4}$ over time or the process can be accelerated by bubbling oxygen through the solution. It will remain chelated to the DOTA-3. This can then purified with HPLC to extract the [tin-117m]-DOTA-BASS or [tin-117m]-DOTA-J11.

Alternatively, aminobenzyl DOTA-4 can be used to bind tin$^{+4}$ to the BASS or J11. The DOTA-4 has all four carboxylic acid groups available to bind to tin. Tin-117m in the +4 state is reacted with aminobenzyl DOTA at elevated temperatures, about 140° C., for 15 minutes to bind the tin to the DOTA-4. This can be conducted in a microwave. The mixture is then purified using HPLC and the tin-117m aminobenzyl DOTA is reacted with thiophosgene to convert the amine to a thiocyanate.

The BASS and J11 are modified by adding an amine group. This compound is simply mixed with the [tin-117m]-cyanothiobenzyl DOTA to form [tin-117m]-DOTA-benzyl-HNCSNH (isothiocyanato)-BASS or [tin-117m]-DOTA-benzyl-HNCSNH(isothiocyanato)-J11. This can then be purified further with HPLC.

The tin conjugated somatostatin receptor binding compound formed as previously described is then used as a treatment for Gastroenteropancreatic Neuroendocrine tumors (GEP-NETS), as well as other cancers which are characterized by the presence of somatostatin receptors, including ovarian cancer. The amount of the tin-117m conjugated somatostatin receptor binding compound will depend on the intended radiation dosage.

The actual dosage will depend on the particular cancer being treated, as well as the individual. Generally, the radiation dosage administered will be from about 0.5 to 200 millicuries, or 0.5 to 100 millicuries, or 0.5 to about 32 millicuries, or 0.5 to 20 millicuries, or 0.5 to 15 millicuries, or 0.5 to 12 millicuries, or 0.5 to 5 millicuries. Within these ranges, one can effectively destroy cancer cells and shrink or destroy tumors while minimizing necrosis of non-cancer cells.

Dosages within these ranges have a hormesis effect where only the cancer cells are destroyed and surrounding cells are actually enhanced, possibly through the stimulation of the immune system. At the lower dosages, 0.5 to 5 millicuries, the tin-117m somatostatin receptor binding compound operates through apoptosis; in other words, accelerating apoptosis of existing apoptotic cells while leaving healthy cells relatively undamaged. At higher (around 100 mCi) dosages the tin-117m can cause necrosis of cells within 290 microns of the tin atom. Accordingly, depending on the desired effect, one can destroy primarily only apoptotic cells or destroy all cells within 290 microns of the tin-117m.

The tin-117m bound to the somatostatin receptor binding compound is preferably administered intravenously. This can be injected intravenously over a period of 20 minutes or more in a 100 ml physiological saline solution. In order to reduce radiation exposures to kidneys, positively charged amino acids can be administered before and during administration of the radioisotope, followed with repeated administrations on subsequent post therapy days.

Once administered, the tin-117m will effectively cause apoptosis or necrosis of the cancerous tissue. As it has an effective range of 290 microns, adjacent non-cancerous tissue should not be negatively impacted.

As the tin-117m has a half life of 14 days, this will provide effective therapy for up to about 4 weeks. This treatment can be repeated as necessary, and can be used in conjunction with other chemotherapeutic agents.

Further, as the tin-117m is also a gamma emitter, localization of the tin-117m can be easily detected, allowing one to determine the locus of tumors.

This has been a description of the present invention along with the preferred method of practicing the present invention.

However, the invention itself should only be defined by the appended claims, wherein we claim:

1. A method of treating a patient having a tumor having somatostatin receptors comprising:
   administering to said patient an effective amount of tin-117m-benzyl-isothiocyanato-DOTA-TATE.

2. The method of claim 1, wherein the effective amount of tin-117m-benzyl-isothiocyanato-DOTA-TATE is from about 0.5 millicuries to about 200 millicuries.

3. The method of claim 1, wherein the effective amount of tin-117m-benzyl-isothiocyanato-DOTA-TATE is from about 0.5 millicuries to about 100 millicuries.

4. The method of claim 1, wherein the effective amount of tin-117m-benzyl-isothiocyanato-DOTA-TATE is from about 0.5 millicuries to about 32 millicuries.

5. The method of claim 1, wherein the effective amount of tin-117m-benzyl-isothiocyanato-DOTA-TATE is from about 0.5 millicuries to about 20 millicuries.

6. The method of claim 1, wherein the effective amount of tin-117m-benzyl-isothiocyanato-DOTA-TATE is from about 0.5 millicuries to about 15 millicuries.

7. The method of claim 1, wherein the effective amount of tin-117m-benzyl-isothiocyanato-DOTA-TATE is from about 0.5 millicuries to about 12 millicuries.

8. The method of claim 1, wherein the effective amount of tin-117m-benzyl-isothiocyanato-DOTA-TATE is from about 0.5 millicuries to about 5 millicuries.

9. The method of claim 1, wherein the tin-117m-benzyl-isothiocyanato-DOTA-TATE is administered intravenously.

10. The method of claim 1, further comprising repeating the administering to said patient an effective amount of tin-117m-benzyl-isothiocyanato-DOTA-TATE after passage of a time period.

11. The method of claim 10, wherein the time period is about 4 weeks.

* * * * *